United States Patent [19]

Evertz et al.

[11] Patent Number: 5,496,902
[45] Date of Patent: Mar. 5, 1996

[54] CATALYST SYSTEMS FOR THE POLYMERIZATION OF $C_2$-$C_{10}$-ALK-1-ENES

[75] Inventors: Kaspar Evertz, Schifferstadt; Ruerger Schlund, Mannheim; Guenther Schweier, Friedelsheim, all of Germany; Hans Brintzinger, Tägerwilen, Switzerland; Werner Roell, Konstanz, Germany; Peter Jutzi, Bielefeld, Germany; Ingrid Mieling, Ochtrup, Germany; Winfried Mengele, Konstanz, Germany

[73] Assignee: BASF Aktiengesellschaft, Ludwigshafen, Germany

[21] Appl. No.: 244,747

[22] PCT Filed: Mar. 23, 1993

[86] PCT No.: PCT/EP93/00694

§ 371 Date: Jun. 13, 1994

§ 102(e) Date: Jun. 13, 1994

[87] PCT Pub. No.: WO93/20113

PCT Pub. Date: Oct. 14, 1993

[30] Foreign Application Priority Data

Apr. 3, 1992 [DE] Germany .................. 42 11 086.6

[51] Int. Cl.$^6$ .................................................. C08F 4/642
[52] U.S. Cl. .................. 526/127; 526/160; 502/102; 502/103; 502/117
[58] Field of Search ................... 502/104, 107, 502/110, 112, 117, 154, 102, 103; 526/127, 160, 150

[56] References Cited

U.S. PATENT DOCUMENTS 4,794,096  12/1988  Ewen ...................... 502/117

FOREIGN PATENT DOCUMENTS 302424  2/1989  European Pat. Off. .
3726067  2/1989  Germany ................ 526/160

OTHER PUBLICATIONS

Siemeling et al., "Trinuclear Homo–and Heterometallic Complexes of a Doubly Bridged Cyclopentadienyl Ligand," *Chemische Berichte*, 125, pp. 31–35 (1992).

*Primary Examiner*—Romulo H. Delmendo
*Attorney, Agent, or Firm*—Keil & Weinkauf

[57] ABSTRACT

Catalyst systems for the polymerization of $C_2$-$C_{10}$-alk-1-enes contain, as active components, a) a metallocene complex of the general formula I

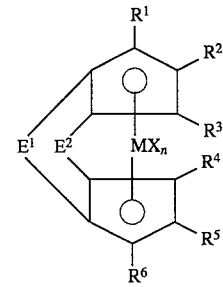

where M is a metal of the subgroup III, IV or v of the Periodic Table of elements or a metal selected from the group consisting of the lanthanides, X is fluorine, chlorine, bromine, iodine, hydrogen, $C_1$–$C_{10}$-alkyl, $C_6$–$C_{15}$-aryl or —$OR^7$, $R^7$ is $C_1$–$C_{10}$-alkyl, $C_6$–$C_{15}$-aryl, alkylaryl, arylalkyl, fluoroalkyl or fluoroaryl, in each case having 1 to 10 carbon atoms in the alkyl radical and 6 to 20 carbon atoms in the aryl radical, n is the valency of M minus two, $R^1$ to $R^6$ are each hydrogen, $C_1$–$C_{10}$-alkyl, 5-membered to 7-membered cycloalkyl which in turn may carry $C_1$–$C_{10}$-alkyl as a substituent, $C_6$–$C_{15}$-aryl or arylalkyl, where two adjacent radicals together may furthermore form a cyclic group of 4 to 15 carbon atoms, or $Si(R^8)_3$, $R^8$ is $C_1$–$C_{10}$-alkyl, $C_6$–$C_{15}$-aryl or $C_3$–$C_{10}$-cycloalkyl, $E^1$ and $E^2$ are independent of one another and are each $Si(R^9)_2$, $Ge(R^9)_2$, $Sn(R^9)_2$ or $C(R^9)_2$—$C(R^9)_2$ and $R^9$ is $C_1$–$C_{10}$-alkyl, $C_3$–$C_{10}$-cycloalkyl or $C_6$–$C_{15}$-aryl, and b) an open-chain or cyclic alumoxane compound of the general formula II or III

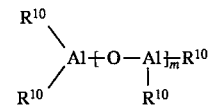

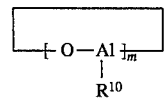

where $R^{10}$ is $C_1$–$C_4$-alkyl and m is an integer of from 5 to 30.

6 Claims, No Drawings

CATALYST SYSTEMS FOR THE POLYMERIZATION OF $C_2$-$C_{10}$-ALK-1-ENES

The present invention relates to catalyst systems for the polymerization of $C_2$–$C_{10}$-alk-1-enes, containing, as active components, a) a metallocene complex of the general formula I

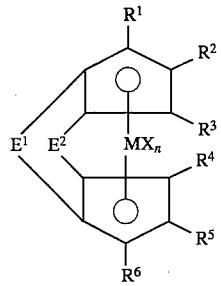

where

M is a metal of the subgroup III, IV or V of the Periodic Table of elements or a metal selected from the group consisting of the lanthanides, X is fluorine, chlorine, bromine, iodine, hydrogen, $C_1$–$C_{10}$-alkyl, $C_6$–$C_{15}$-aryl or —$OR^7$, $R^7$ is $C_1$–$C_{10}$-alkyl, $C_6$–$C_{15}$-aryl, alkylaryl, arylalkyl, fluoroalkyl or fluoroaryl, in each case having 1 to 10 carbon atoms in the alkyl radical and 6 to 20 carbon atoms in the aryl radical, n is the valency of M minus two, $R^1$ to $R^6$ are each hydrogen, $C_1$–$C_{10}$-alkyl, 5-membered to 7-membered cycloalkyl which in turn may carry $C_1$–$C_{10}$-alkyl as a substituent, $C_6$–$C_{15}$-aryl or arylalkyl, where two adjacent radicals together may furthermore form a cyclic group of 4 to 15 carbon atoms, or $Si(R^8)_3$, $R^8$ is $C_1$–$C_{10}$-alkyl, $C_6$–$C_{15}$-aryl or $C_3$–$C_{10}$-cycloalkyl, $E^1$ and $E^2$ are independent of one another and are each $Si(R^9)_2$, $Ge(R^9)_2$, $Sn(R^9)_2$ or $C(R^9)_2$–$C(R^9)_2$ and $R^9$ is $C_1$–$C_{10}$-alkyl, $C_3$–$C_{10}$-cycloalkyl or $C_6$–$C_{15}$-aryl, and b) an open-chain or cyclic alumoxane compound of the formula II or III

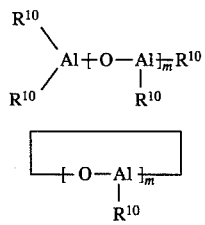

where $R^{10}$ is $C_1$–$C_4$-alkyl and m is an integer of from 5 to 30.

The present invention furthermore relates to a process for the preparation of metallocene complexes of the formula I, the use of a catalyst system for the preparation of polyalk-1-enes, processes for the preparation of polyalk-1-enes with the aid of these catalyst systems and the polyalk-1-enes obtainable thereby.

Metallocene dichlorides having a single dimethylsilyl bridge have already been widely mentioned in the patent literature and, in conjunction with alumoxanes, constitute olefin polymerization catalysts which are defined in molecular terms. Owing to the bridging of the cyclopentadienyl ligands, the ligand skeletons are stereorigid and result in high stereospecificity in the e-olefin polymerization, as disclosed in, for example, EP-A 302 424.

However, precisely at the technically interesting higher temperatures, the ligand skeleton may lose stereo-rigidity, so that the stereospecificity decreases.

It is an object of the present invention to provide catalyst systems which have high stereorigidity and, in conjunction with alumoxanes, possess the high productivities typical for metallocene catalysts.

We have found that this object is achieved by the catalyst systems defined at the outset for the preparation of polyalk-1-enes. We have also found processes for the preparation of metallocene complexes of the formula I, the use of the catalyst systems for the preparation of polyalk-1-enes, processes for the preparation of polyalk-1-enes with the aid of these catalyst systems and the polyalk-1-enes obtainable thereby.

The novel catalyst systems contain, as active components, inter alia one or more complexes of the formula I

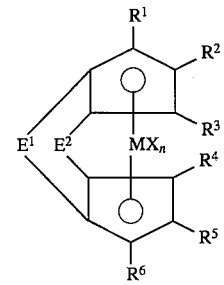

where M is a metal of the subgroup III, IV or V of the Periodic Table of elements or a metal from the group consisting of lanthanides, preferably a metal of the subgroup IV or V, in particular titanium, zirconium or hafnium. X is halogen, preferably chlorine, hydrogen, $C_1$–$C_{10}$-alkyl, preferably linear alkyl of 1 to 4 carbon atoms, in particular methyl or ethyl, $C_6$–$C_{15}$-aryl, preferably phenyl, or —$OR^7$, $R^7$ being $C_1$–$C_{10}$-alkyl, $C_6$–$C_{15}$-aryl, alkylaryl, arylalkyl, fluoroalkyl or fluoroaryl having in each case 1 to 10 carbon atoms in the alkyl radical and 6 to 20 carbon atoms in the aryl radical.

$R^1$ to $R^6$ independently of one another are each preferably hydrogen, $C_1$–$C_{10}$-alkyl, preferably $C_1$–$C_4$-alkyl, 5-membered to 7-membered cycloalkyl which in turn may carry $C_1$–$C_{10}$-alkyl as a substituent, $C_6$–$C_{15}$-aryl, preferably phenyl, or arylalkyl. It is also possible for two adjacent radicals, ie $R^1$ and $R^2$ or $R^2$ and $R^3$ and $R^4$ and $R^5$ or $R^5$ and $R^6$, together to form cyclic groups of 4 to 15 carbon atoms which may also be aromatic; it is preferable here for two adjacent radicals to form a six-membered ring, particularly so that an indenyl or tetrahydroindenyl radical results . Furthermore, $R^1$ to $R^6$ may be $Si(R^8)_3$, where $R^8$ is $C_1$–$C_{10}$-alkyl, $C_6$–$C_{15}$-aryl or $C_3$–$C_{10}$-cycloalkyl. Particularly suitable compounds of the formula I are those in which $R^1$ to $R^6$ are chosen so that symmetrical compounds are formed, ie., for example, $R^1$ and $R^4$ are identical as are $R^2$ and $R^5$ and $R^3$ and $R^6$.

$E^1$ and $E^2$ may be identical or different and are each $Si(R^9)_2$, $Ge(R^9)_2$, $Sn(R^9)_2$ or $C(R^9)_2$—$C(R^9)_2$, $Si(R^9)_2$ being preferred. $R^9$ is $C_1$–$C_{10}$-alkyl, preferably $C_1$–$C_4$-alkyl, in particular methyl, $C_3$–$C_{10}$-cycloalkyl, preferably $C_5$- or $C_6$-cycloalkyl, or $C_6$–$C_{15}$-aryl, preferably phenyl.

In a preferred process for the preparation of metallocene complexes of the general formula I, a compound of the formula IV

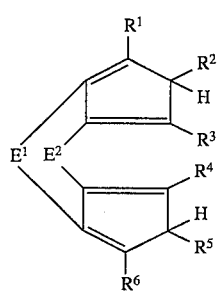

is reacted with a metallizing agent, such as an alkyllithium, preferably butyllithium, or potassium hydride, preferably in an aliphatic hydrocarbon as solvent, in particular in pentane or hexane, to give a compound having bismetallized ligands. $MX_{n+2}$ is then added at from −50° to 100° C. This reaction step can be carried out in the presence or absence of a solvent. The reaction in an aromatic hydrocarbon as a solvent, in particular in toluene, is preferred.

The preparation of the compounds of the formula IV is known per se to the skilled worker and is described in, for example, Organometallics 10 (1991), 1787–1793. A cyclopentadienyllithium compound

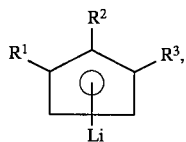

is preferably chosen as a starting compound and is reacted with dihalogenated $E^1$ or $E^2$ and butyllithium is then preferably added in order to obtain compounds of the general formula IV by dimerization. A process for the preparation of compounds of the formula IV in which $E^1$ and $E^2$ are different is described in, for example, Metallorg. Khim. 4 (1991), 2, 292–298.

The metallocene complexes may also be present in cationic form, as described in EP-A 277 003 and EP-A 277 004.

In addition to the metallocene complexes, the novel catalyst systems also contain oligomeric alumina compounds.

For example, open-chain or cyclic alumoxane compounds of the general formula II or III

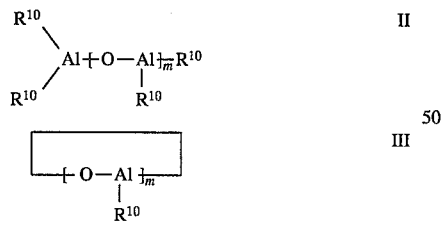

where $R^{10}$ is $C_1$–$C_4$-alkyl, preferably methyl or ethyl, and m is an integer from 5 to 30, preferably from 10 to 25, are suitable.

The preparation of these oligomeric alumoxane compounds is usually carried out by reacting a solution of a trialkylaluminum with water and is described in, inter alia, EP-A 284 708 and US-A 4,794,096.

As a rule, the oligomeric alumoxane compounds obtained are in the form of mixtures of both linear and cyclic chain molecules of different lengths, so that m is to be regarded as an average value. The alumoxane compound may also be present as a mixture with other metal alkyls, preferably with alkylaluminums.

It has proven advantageous if the atomic ratio of aluminum from the oligomeric alumina compound to the metal M from the metallocene complex is from 10:1 to $10^6$:1, preferably from 10:1 to $10^4$:1.

The components of the novel catalyst system can be introduced into the polymerization reactor individually in any order or as a mixture.

With the aid of these catalyst systems it is possible to prepare polymers of alk-1-enes. These include homo- and copolymers of $C_2$–$C_{10}$-alk-1-enes, the monomers used preferably being ethylene, propylene, but-1-ene, pent-1-ene and hex-1-ene.

The preparation of these polymers can be carried out in the conventional reactors used for polymerization of alkenes, either batchwise or, preferably, continuously. Suitable reactors include continuous stirred kettles, and a plurality of stirred kettles connected in series may also be used.

The polymerization conditions are in principle not critical; pressures of from 0.5 to 3,000, preferably from 1 to 80, bar and temperatures of from −50° to +300° C., preferably from −20° to 100° C., have proven suitable.

Polymerization reactions with the aid of the novel catalyst systems can be carried out in the gas phase, in a suspension, in liquid monomers or in inert solvents. In the polymerization in solvents, in particular liquid hydrocarbons, such as benzene or toluene, are used. Polymers having good performance characteristics are also obtainable in the polymerization in the gas phase, in a suspension or in liquid monomers.

The average molecular weight of the polymers formed can be controlled by the methods usually used in polymerization technology, for example by adding regulators, such as hydrogen, or by changing the reaction temperatures. It is possible to prepare both polymers having low average molecular weights and, by reducing the reaction temperature, polymers having higher average molecular weights.

The novel catalyst systems have high productivity, and the polymers prepared with the aid of the novel catalyst systems possess a balanced property spectrum.

EXAMPLES

EXAMPLE 1

Preparation of a zirconium complex of the formula Ia

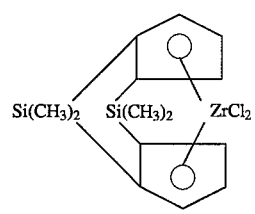

0.2 mol of

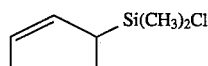

were reacted with 0.2 mol of n-butyllithium in 1,000 ml of pentane at −100° C. to give a compound of the formula IVa

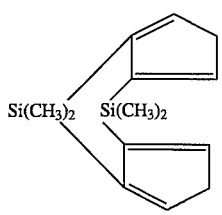

780 mg ($\hat{=}$3.20 mmol) of the compound IVa were dissolved in 40 ml of toluene, and 4 ml of a 1.6 molar solution of n-butyllithium in hexane ($\hat{=}$6.40 mmol) were added. 3.20 mmol of the resulting compound having bismetallized ligands were added dropwise at room temperature to a suspension of 1.82 g ($\hat{=}$7.81 mmol) of $ZrCl_4$ in 100 ml of toluene, a yellow color being observed.

Heating was then carried out for 1 hour at 80° C., the color changing to light brown. After 6 hours, the mixture was allowed to cool to room temperature, undissolved material was filtered off and the solid residue was washed with toluene ( 2×20 ml ) and the solvent removed completely under greatly reduced pressure. The residue was extracted with 200 ml of hexane and the yellow suspension formed was evaporated to half its volume and cooled to −30° C. A colorless powder was isolated.

Yield:544 mg ( 42% ) Melting point: 159° C. (decomposition) Slow decomposition occurred in the air. Analytical data for compound Ia:

$^1$H-NMR ($CDCl_3$): $\delta$=0.54, 0.92 (2s, 2×12H, 2×$CH_3$) , 6.45 (t, $^3J$=2.35 Hz, 4H, H-5, H-11, H-5', H-11'), 6.94 (d, $^3j$=2.35 Hz, 8H, H-4, H-6, H-10, H-12, H-4', H-6', H-10', H-12').

$^{13}C\{^1H\}$-HMR ($CDCl_{32}$): $\delta$=−4.46, 2.27 (2×$CH_3$), 114.88 (C-5, C-11, C-5', C-11'), 116.01 (C-4, C-6, C-10, C-12, C-4', C-6', C-10', C-12'), 139.80 (C-1, C-3, C-7, C-9, C-1', C-3', C-7', C-9').

$^{29}Si$-NMR ($CDCl_3$): $\delta$=−17.10.

$C_{14}H_{16}Cl_2Si_2Zr_1$ (404.3) Calculated C 41.55 H 4.45 Found C 40.74 H 4.59

EXAMPLES 2 TO 8

Preparation of polyethylene ( PE) using Ia 450 ml of toluene were initially taken in a 1 l glass autoclave and heated to various temperatures, and 8.6 ml ($\hat{=}$13.8 mmol) of methylalumoxane solution (MAO) (1.6 molar in toluene) were added. Various amounts of a 0.0013 molar solution of Ia in toluene were then added. Ethylene was then forced in under various pressures. After various polymerization times, the pressure was let down and the PE formed was freed from adhering solvent by expelling the toluene with steam and was dried.

In Examples 2 to 5, the stirrer speed in the autoclave remained at 250 rpm, whereas in Examples 6 to 8 it was increased from 250 rpm to 350 rpm.

The experimental conditions and the properties of the polymers formed are summarized in Table 1.

The weight average molecular weight $\bar{M}_w$ and the number average molecular weight $\bar{M}_n$ were determined by gel permeation chromatography.

TABLE 1

| Example | MAO [ml] | MAO [mmol] | Ia [mg] | Ia [mmol] | Atomic ratio of Al from MAO to Zr from Ia | Temperature [°C.] | Pressure [bar] | Polymerization time [minutes] |
|---|---|---|---|---|---|---|---|---|
| 2 | 8.6 | 13.8 | 1.12 | 1.38 · 10$^{-3}$ | 10,000:1 | 110 | 6 | 60 |
| 3 | 8.6 | 13.8 | 1.12 | 1.38 · 10$^{-3}$ | 10,000:1 | 80 | 6 | 30 |
| 4 | 8.6 | 13.8 | 1.12 | 1.38 · 10$^{-3}$ | 10,000:1 | 50 | 6 | 60 |
| 5 | 8.6 | 13.8 | 1.12 | 1.38 · 10$^{-3}$ | 10,000:1 | 110 | 10 | 60 |
| 6 | 8.6 | 13.8 | 1.12 | 1.38 · 10$^{-3}$ | 10,000:1 | 80 | 6 | 30 |
| 7 | 8.6 | 13.8 | 1.12 | 1.38 · 10$^{-3}$ | 10,000:1 | 80 | 6 | 60 |
| 8 | 8.6 | 13.8 | 1.12 | 1.38 · 10$^{-3}$ | 10,000:1 | 80 | 10 | 60 |

| Example | Yield [g PE] | [g PE/h · g Ia] | [g PE/h · g Zr] | $\bar{M}_w$ [g/mol] | $\bar{M}_n$ [g/mol] | $\bar{M}_w/\bar{M}_n$ |
|---|---|---|---|---|---|---|
| 2 | 27.9 | 24.9 · 10$^3$ | 0.11 · 10$^6$ | 31,800 | 13,000 | 2.45 |
| 3 | 11.8 | 21.1 · 10$^3$ | 0.09 · 10$^6$ | 83,500 | 29,500 | 2.83 |
| 4 | 6.4 | 5.7 · 10$^3$ | 0.025 · 10$^6$ | — | — | — |
| 5 | 50.4 | 45.0 · 10$^3$ | 0.20 · 10$^6$ | 43,000 | 15,000 | 2.86 |
| 6 | 23.1 | 41.3 · 10$^3$ | 0.18 · 10$^6$ | 103,400 | 29,500 | 3.51 |
| 7 | 21.6 | 38.6 · 10$^3$ | 0.17 · 10$^6$ | 113,200 | 48,300 | 2.34 |
| 8 | 20.8 | 74.3 · 10$^3$ | 0.33 · 10$^6$ | 131,900 | 51,000 | 2.59 |

EXAMPLE 9

Preparation of polypropylene (PP) using Ia 20 g of PP grit were introduced into a 10 l autoclave at room temperature with nitrogen counter-current. 9.4 ml ($\hat{=}$14 mmol) of methylalumoxane solution (MAO) (1.53 molar in toluene) were added with the nitrogen counter-current while stirring (500 rpm). A solution of 7.1 mg ($\hat{=}$0.017 mmol) of Ia which had been preactivated with 400 molar equivalents (based on Zr) of methylalumoxane solution (1.5 molar in toluene) while stirring for 15 minutes at room temperature was then added, likewise with a nitrogen counter-current. After the condensation of 7 l of liquid propylene, stirring was carried out for 5 minutes at room temperature, after which the temperature was increased to 50° C., resulting in a pressure increase to about 20 bar, and these polymerization conditions were kept constant for 90 minutes. Tacky polypropylene was obtained.

| MAO | | Ia | | Atomic ratio of Al from MAO and Zr from Ia | Yield | Productivity | |
|---|---|---|---|---|---|---|---|
| [ml] | [mmol] | [mg] | [mmol] | | [g] | [g PP/g Zr] | [g PP/g Ia] |
| 9.4 | 14.04 | 7.1 | 0.017 | 1200:1 | 110 | 68,968 | 15,493 |

EXAMPLE 10

Preparation of a zirconium complex of the formula Ib

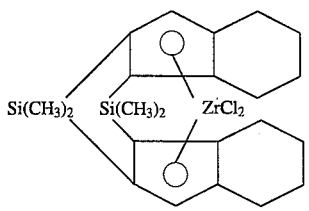

Ib

Tetrahydroindene was reacted with n-butyllithium

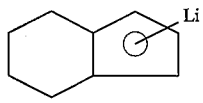

100 ml of tetrahydrofuran (THF) were added to 7.24 g ($\hat{=}$ 57.4 mmol) of this compound, after which 3.5 g ($\hat{=}$28 mmol) of $Si(CH_3)_2Cl_2$ were added while cooling with ice. The reddish brown, clear solution was stirred for 4 hours. Thereafter, 100 ml of diethyl ether were added and extraction by shaking was carried out twice with 50 ml of saturated aqueous $NH_4Cl$ solution in each case. The organic phase was washed with 50 ml of water, dried with $MgSO_4$ and then completely freed from the solvent under reduced pressure.

8 g of the compound

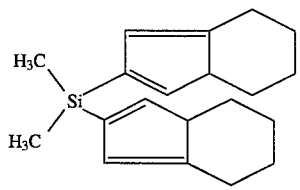

were obtained in this manner as viscous oil (molecular ion peak at m/e 296). This was dissolved in 100 ml of pentane, the solution was cooled to 0° C. and conversion into the dilithium salt was effected by adding 34.2 ml ($\hat{=}$55 mmol) of a 1.6 molar solution of butyllithium in hexane. The dilithium salt was filtered off, washed with twice 10 ml of pentane and dried under greatly reduced pressure.

The dilithium salt (8.0 g, 26 mmol) thus obtained was suspended in 50 ml of THF, and 3.3 g ($\hat{=}$26 mmol) of $(CH_3)_2SiCl_2$ were added while cooling with ice. Stirring was carried out for 4 hours, after which the solvent was completely removed under reduced pressure. The residue was extracted with five times 20 ml of pentane. Evaporating down the extract gave 8.4 g of a compound of the formula IVb

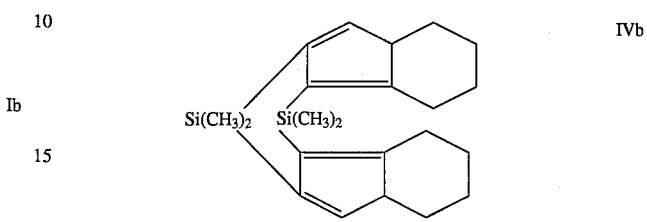

as a white, rubber-like mass (molecular ion peak at m/e 352).

The latter was suspended in 50 ml of pentane, 30 ml ($\hat{=}$48 mmol) of a 1.6 molar solution of n-butyllithium in hexane were added while cooling with ice and stirring was then carried out for 24 hours at room temperature. The precipitated dilithium salt was filtered off, was washed twice with 10 ml of pentane and dried under greatly reduced pressure. 6.9 g ($\hat{=}$18.9 mmol) of this dilithium salt were mixed with 4.8 g ($\hat{=}$20.8 mmol) of solid $ZrCl_4$; 75 ml of toluene were added at room temperature. The resulting brown suspension was stirred for 20 hours. Thereafter, the solvent was completely removed under greatly reduced pressure and the solid residue was extracted with about 200 ml of pentane in a Soxhlet apparatus. The extract obtained was evaporated down to about 40 ml. The resulting slightly greenish solid was filtered off, washed with a little pentane and dried under greatly reduced pressure. 2.6 g (27% of theory) of a mixture of Ib with other complex isomers were thus obtained.

The racemic complex Ib was isolated from this isomer mixture by diffusion-induced crystallization from toluene/diethyl ether. Repetition of this purification process three times gave 0.6 g of pure rac-Ib. Analytical data for Ib $^1$H-NMR ($C_6D_6$): δ=0.32 (s, 6H), 0.60 (s, 6H), 1.29–2.96 (m, 16H), 6.52 (s, 2H)

$C_{22}H_{30}Cl_2Si_2Zr$ (512.8) Calculated C 51.50 H 5.90 Found C 51.04 H 5.56

EXAMPLE 11

Preparation of polypropylene (PP) using rac-Ib 350 ml of toluene were initially taken in a 1 l autoclave at 50° C. and 5 ml of a 10% strength by weight solution of methylalumoxane in toluene ($\hat{=}$7.7 mmol) and 3.2 mg ($\hat{=}$6.25·10$^{-6}$ mol) of Ib, dissolved in 20 ml of toluene, were added. Stirring was carried out for 30 minutes, after which propylene was forced in at a pressure of 2 bar. After 9 hours, the reaction product was added to a mixture of 1 l of methanol and 10 ml of concentrated HCl and the precipitate was filtered off, washed with methanol and dried for 2 hours at 50° C. 56 g of crystalline PP were obtained.

The weight average molecular weight $\bar{M}_w$ was 14,935, the number average molecular weight $\bar{M}_n$ was 9,371 and the ratio $\bar{M}_w/\bar{M}_n$ was 1.6 ($\bar{M}_w$ and $\bar{M}_n$ were determined by gel permeation chromatography).

The melting point was 116.5° C. determined by DSC measurements (Differential Scanning Calorimetry). Isotacticity: 75.2% mmmm pentads, measured by $^{13}$C-NMR.

We claim:

1. A catalyst system for the polymerization of $C_2$-$C_{10}$-alk-1-enes, containing, as active components, a) a metallocene complex of the formula I

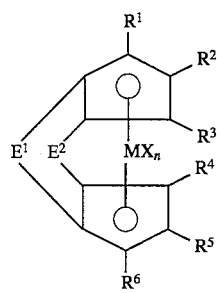

where

M is a metal of the subgroup III, IV or V of the Periodic Table of elements or a metal selected from the group consisting of the lanthanides, X is fluorine, chlorine, bromine, iodine, hydrogen, $C_1$–$C_{10}$-alkyl, $C_6$–$C_{15}$-aryl or —$OR^7$, $R^7$ is $C_1$–$C_{10}$-alkyl, $C_6$–$C_{15}$-aryl or alkylaryl, arylalkyl, fluoroalkyl or fluoroaryl, 1 to 10 carbon atoms in each alkyl radical and 6 to 20 carbon atoms in each aryl radical, n is the valency of M minus two, $R^1$ to $R^6$ are each hydrogen, $C_1$–$C_{10}$-alkyl, 5-membered to 7-membered cycloalkyl which in turn may carry $C_1$–$C_{10}$-alkyl as a substituent, $C_6$–$C_{15}$-aryl or arylalkyl, where two adjacent radicals together may furthermore form a cyclic group of 4 to 15 carbon atoms, or $Si(R^8)_3$, $R^8$ is $C_1$–$C_{10}$-alkyl, $C_6$–$C_{15}$-aryl or $C_3$–$C_{10}$-cycloalkyl, $E^1$ and $E^2$ are independent of one another and are each $Si(R^9)_2$, $Ge(R^9)_2$, $Sn(R^9)_2$ or $C(R^9)_2$—$C(R^9)_2$ and $R^9$ is $C_1$–$C_{10}$-alkyl, $C_3$–$C_{10}$-cycloalkyl or $C_6$–$C_{15}$-aryl, and b) an open-chain or cyclic alumoxane compound of the formula II or III

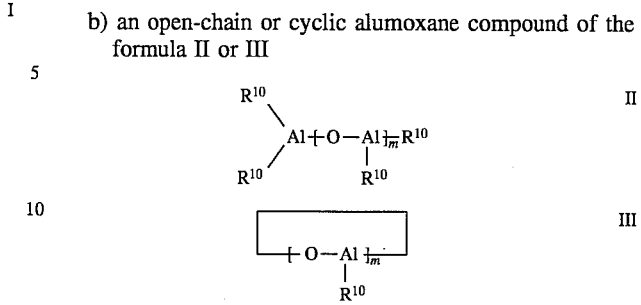

where $R^{10}$ is $C_1$–$C_4$-alkyl and m is an integer of from 5 to 30.

2. A catalyst system as defined in claim 1, wherein M is titanium, zirconium or hafnium.

3. A catalyst system as defined in claim 1 or 2, wherein $E^1$ and $E^2$ are each $Si(R^9)_2$.

4. A process for the preparation of a polymer of $C_2$–$C_{10}$-alk-1-enes which comprises: contacting the alk-1-enes at from 0.5 to 3,000 bar and from −50° to 300° C. with the catalyst system defined in claim 1.

5. A process for the preparation of a polymer of $C_2$–$C_{10}$-alk-1-enes which comprises: contacting the alk-1-enes at from 0.5 to 3,000 bar and from −50° to 300° C. with the catalyst system defined in claim 2.

6. A process for the preparation of a polymer of $C_2$–$C_{10}$-alk-1-enes which comprises: contacting the alk-1-enes at from 0.5 to 3,000 bar and from −50° to 300° C. with the catalyst system defined in claim 3.

* * * * *

UNITED STATES PATENT AND TRADEMARK OFFICE
CERTIFICATE OF CORRECTION

PATENT NO. : 5,496,902
DATED : March 5, 1996
INVENTOR(S) : EVERTZ et al.

It is certified that error appears in the above-indentified patent and that said Letters Patent is hereby corrected as shown below:

On the title page, item [75], the first name of the second listed inventor should be --Rueger--.

Column 9, claim 1, line 22, before "1 to 10" insert --having--.

Signed and Sealed this

Twenty-fifth Day of June, 1996

Attest:

BRUCE LEHMAN

*Attesting Officer*      *Commissioner of Patents and Trademarks*